United States Patent [19]
Ikebe et al.

[11] Patent Number: 4,877,018
[45] Date of Patent: Oct. 31, 1989

[54] DEVICE FOR DEODORIZING AND DRYING PORTION BETWEEN TOES

[75] Inventors: Takashi Ikebe, Sakai; Takigawa: Masuhiko, Osaka, both of Japan

[73] Assignee: Masuhiko Takigawa, Osaka, Japan

[21] Appl. No.: 243,042

[22] Filed: Sep. 12, 1988

[30] Foreign Application Priority Data

Sep. 21, 1987 [JP] Japan ............................ 62-144783[U]

[51] Int. Cl.$^4$ ............................................... A61F 5/00
[52] U.S. Cl. ..................................... 128/81 R; 36/94; 128/893; 604/293
[58] Field of Search ...................... 128/81 R, 893, 894; 132/73; 604/293; 36/71, 77 R, 94

[56] References Cited

U.S. PATENT DOCUMENTS

| 2,173,528 | 9/1939 | Beale | 604/293 X |
| 2,451,906 | 10/1948 | Berman | 604/293 |
| 2,506,308 | 5/1950 | Maynier | 132/73 X |
| 2,740,207 | 4/1956 | Starensier | 604/293 X |
| 3,110,306 | 11/1963 | Posher | 128/81 R |
| 3,128,763 | 4/1964 | Langenfeld et al. | 604/293 X |
| 3,490,453 | 1/1970 | Ogden | 128/81 R X |
| 3,943,922 | 3/1976 | Umeda | 128/81 R |
| 4,207,880 | 6/1980 | Zinkovich | 128/81 R |

FOREIGN PATENT DOCUMENTS

| 1024294 | 3/1953 | France | 132/73 |
| 1027346 | 5/1953 | France | 132/73 |
| 137189 | 5/1930 | Switzerland | 128/81 R |
| 279366 | 10/1927 | United Kingdom | 128/81 R |
| 365572 | 7/1930 | United Kingdom | 132/73 |

Primary Examiner—Edgar S. Burr
Assistant Examiner—Moshe I. Cohen
Attorney, Agent, or Firm—Wenderoth, Lind & Ponack

[57] ABSTRACT

A device for deodorizing and drying a portion between toes used by putting it between toes.

The device comprises two rod-shaped flexible fibrous elements or layers formed of a large number of fibers disposed parallel to the longitudinal axis of said layers, an air- and water-permeable flexible shell member being wound around said flexible fibrous layers such that a cavity is formed between the upper fibrous layer and the lower fibrous layer, and particulate substances having a hygroscopic function being housed in said cavity in a quantity corresponding to a part of a volume of said cavity.

1 Claim, 2 Drawing Sheets

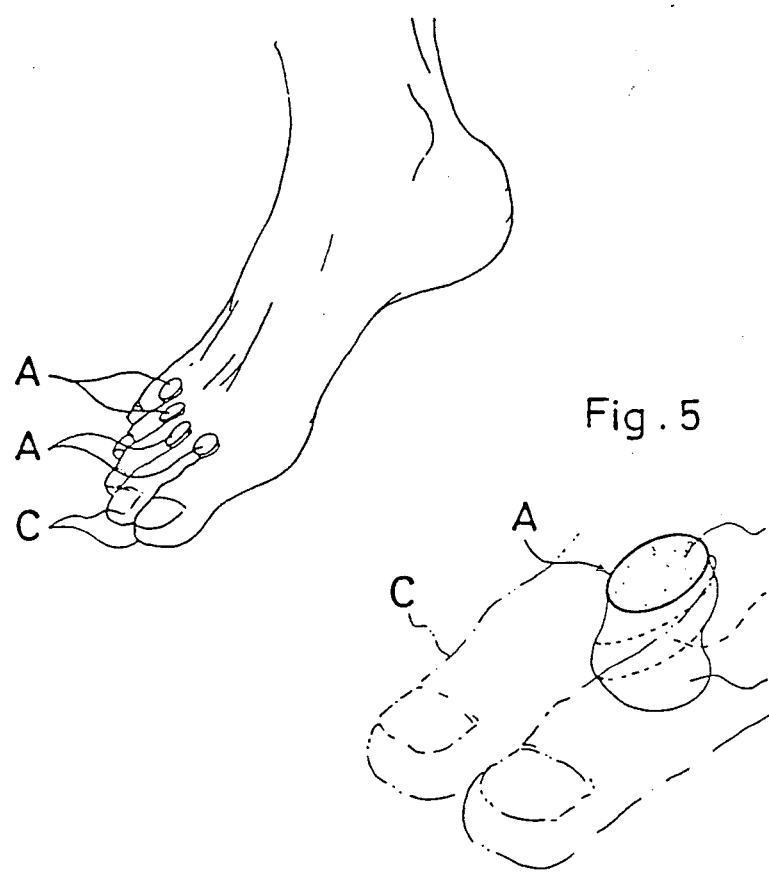
Fig. 4
Fig. 5
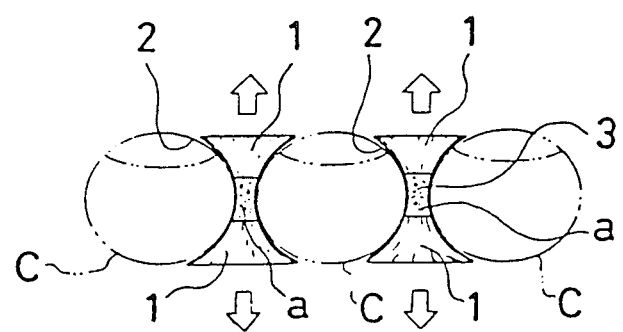
Fig. 6

4,877,018

DEVICE FOR DEODORIZING AND DRYING PORTION BETWEEN TOES

BACKGROUND OF THE INVENTION

1. Field of the Invention

The present invention relates to a device for deodorizing and drying a portion between toes which is capable of keeping the toes in a dry and clean condition such that a bad smell and a ringworm are difficult to generate by putting it between the toes.

2. Prior Art

A device for deodorizing and drying used with putting it between toes has been known by Japanese Patent Laid-Open No. Sho 48-59692, Sho 52-134280, Japanese Utility Model Laid-Open No. Sho 60-81524, Sho 55-168324, Sho 60-49815 and the like.

For example, (1) cotton and sponge are formed in a round rod-like shape or a flat rod-like shape to be put between toes; (2) hygroscopic powders are housed in a cylindrical member formed of urethane foam; (3) a bag, in which activated carbon and the like are housed, is mounted on a ring member, through which a toe is passed, to put said bag in the vicinity of a root of the toe under the condition that a portion between toes is expanded by the ring member; and the like.

Since these are all used by directly putting them in the portion between the toes where a bad smell and ringworm are most easy to generate, it seems that they are more effective than the general device for deodorizing and drying composed as an insole but there are many problems in fact. Accordingly, no practically useful device has been discovered.

For example, in the case of (1), the device for deodorizing and drying is pressed by the toes from both sides to be deformed in a flat shape, whereby the toes are brought into almost close contact to each other, under the condition that the device for deodorizing and drying formed of cotton or sponge is put between the toes. Accordingly, the ventilation through the portion between the toes by the device for deodorizing and drying is possible only in the up and down direction but cotton and sponge do not show the orientation in ventilation, so that the ventilation is remarkably reduced under the condition that the device is surrounded by the toes.

In the case of the device for deodorizing and drying comprising the cylindrical member filled with a hygroscopic substance, such as (2), if the hygroscopic substance is filled in a great quantity, when the device is put between the toes, the compactly filled hygroscopic substance leads to a sense of incongruity. On the contrary, if the hygroscopic substance is filled in a small quantity, it falls to the bottom (side of the back of foot) of the cylindrical member, whereby the portion between the toes can not be effectively deodorized and dried.

In addition, in the case of the device for deodorizing and drying using a hard ring member, such as (3), not only is a sense of incongruity is felt between the toes but also there is the possibility that the toes are injured due to the breakage and the like of the ring member.

In view of the above described disadvantages of the prior arts, it is an object of the present invention to provide a device for deodorizing and drying a portion between toes superior in safety which is capable of keeping a superior ventilation in the up and down direction even under the condition that the device is put between the toes to be deformed in a flat shape. Also, it is an object of the invention to provide a device for effectively dehumidifying and deodorizing the vicinity of the root of toe in spite of using a small quantity of the hygroscopic substance used without giving the sense of incongruity even though the device is used by directly putting between the toes.

SUMMARY OF THE INVENTION

In order to achieve the above described object, the present invention takes the following technical measure. That is to say, a device for deodorizing and drying a portion between toes according to the present invention is a device for deodorizing and drying used by putting it between toes, characterized by flexible fibrous elements or layers formed of a large number of fibers put in order in the longitudinal direction and swarmed in a rodlike shape which are arranged up and down at a suitable interval, an air- and water-permeable flexible shell member being wound around said flexible fibrous layers to form a cavity portion between the upper fibrous layer and the lower fibrous layer, and particulate substances having a hygroscopic function being housed in said cavity portion in a quantity corresponding to a part of a volume of said cavity portion.

The device for deodorizing and drying having the above described construction is used by putting it between the toes and covering it with socks and the like.

Under the condition that the device for deodorizing and drying is put between the toes, the cavity portion forming an intermediate layer between the upper and lower fibrous layers is positioned just in the vicinity of the root of toe, whereby the dehumidification and deodorization by the particulate substances housed in the cavity portion can be effectively conducted.

In addition, immediately after the device for deodorizing and drying is put between the toes the sense of incongruity is slightly felt but the intermediate layer is formed by the cavity portion and the particulate substances are housed in said cavity portion in the suitable quantity, in short, in the quantity corresponding to a part of the volume of the cavity portion with remaining spaces, so that the intermediate layer is easy to deform in a flat shape and the intermediate layer and the upper and lower fibrous layers are gradually smashed from both sides by the toes. As a result, the device for deodorizing and drying is plastically deformed in an almost hand drum-shape in section as a whole, so that the sense of incongruity can be eliminated.

Moreover, even though the device for deodorizing and drying is plastically deformed in an almost hand drum-shape in the above described manner, whereby the toes are almost brought into close contact, the fibers constructing said fibrous layers are all longitudinally orientated in the upper and lower fibrous layers, so that the ventilation in the up and down direction is remarkably superior.

BRIEF DESCRIPTION OF THE DRAWINGS

One preferred embodiment of the present invention is shown in the drawings, in which

FIG. 4 is a diagram showing how to use the device; and

FIGS. 5, 6 are diagrams showing the device in a deformed state between toes.

DETAILED DESCRIPTION OF THE PREFERRED EMBODIMENTS

Figure 1:
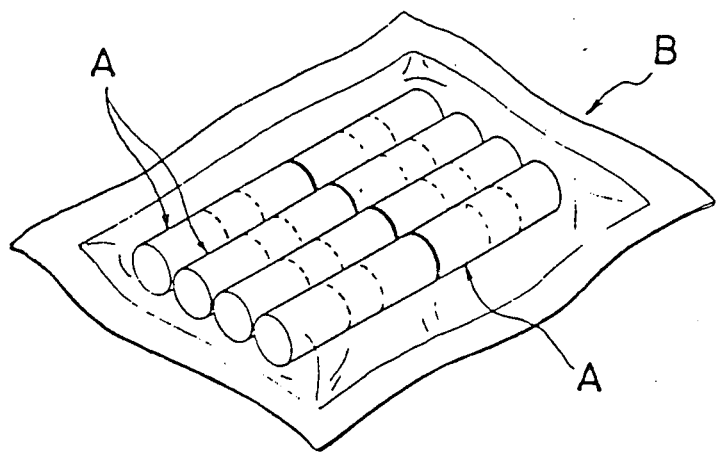
FIG. 1 is a perspective view showing the device for deodorizing and drying a portion between toes packed with 8 pieces thereof as one set.
Figure 2:
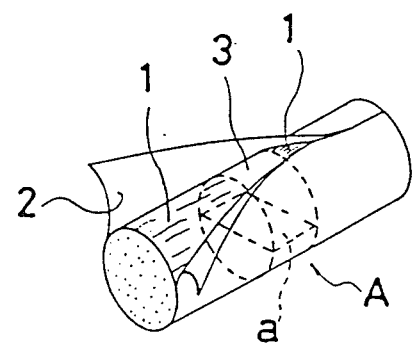
FIG. 2 is a perspective view showing the device for deodorizing and drying a portion between toes after unwinding a part of a shell member.
Figure 3:
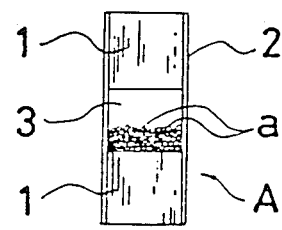
FIG. 3 is a sectional view showing the device for deodorizing and drying a portion between toes.

The preferred embodiments of the present invention are below described with reference to the drawings.

Referring now to the drawings, A designates a device for deodorizing a portion between toes according to the present invention and B designates the condition that said device for deodorizing and drying A is packed in a gas barrier transparent film with eight pieces thereof as one set.

Said device A for deodorizing and drying a portion between toes has a three-layer structure, the flexible fibrous layers 1, 1 formed of a large number of fibers put in order in the longitudinal direction and swarmed in a rod-like shape being arranged up and down at a suitable interval, an air- and water-permeable flexible shell member 2 being wound around said flexible fibrous layers 1, 1 to form a cavity portion 3 as the intermediate layer between the upper and lower fibrous layers 1, 1, and particulate substances a — having a hygroscopic function being housed in said cavity portion 3 in a quantity corresponding to a part (for example about a half of the volume of the cavity portion 3) of the volume of said cavity portion 3.

The particulate substances a — having a hygroscopic function may include substances having also an adsorptive function, such as activated carbon, sepiolite and zeolite, in addition to substances, such as silica gel, having merely the hygroscopic function. They may be used in combination. In particular, sepiolite and zeolite are preferable from the viewpoint of deodorization due to the adsorptive function for ammonia thereof.

Acetic acid series of fiber, such as acetate fiber, are used as the fiber of said respective fibrous layers 1. The fibrous layer 1 may keep the rod-like shape thereof by the shell member 2 wound therearound but in this preferred embodiment the shell member 2 is molded in a rod-like shape before it is wound. Concretely speaking, it is produced by a method similar to a method of producing a cigarette filter, that is, solvents, such as triacetylene, are added to acetic acid series of fiber and the softened fibers are spot-welded among themselves at contact portions to mold in a rod-like shape with the fibers intertwined with each other, the fibers being orientated along an axis shaft line.

For example a paper and the like having a waterproofness are preferably used as the shell member 2 but every other flexible material having an air- and water-permeability may be used.

The above described device A for deodorizing and drying a portion between toes is disposable. For example, every morning a package bag formed of the gas barrier transparent film is broken to take out the new device A for deodorizing and drying and then the taken-out new device A is directly put between the toes C — and then covered with socks and the like, as shown in FIG. 4.

Said device A for deodorizing and drying is flexible and the cavity portion 3 forming the intermediate layer and the upper and lower fibrous layers 1, 1 are smashed from both sides by the toes C — soon after the device A is fitted followed by being plastically deformed so as to show an almost hand drum-like shape in section as a whole, as shown in FIGS. 5, 6, so that the sense of incongruity is eliminated and the device A is difficult to remove also from the portion between the toes C—.

Since the fibers constructing the upper and lower fibrous layers 1, 1 are orientated in the up and down direction, respectively, the ventilation exhibits the orientation, that is, the ventilation in the up and down direction is more notable than that in the lateral direction. Accordingly, the superior ventilation in the up and down direction (in the direction shown by an arrow in FIG. 6) can be kept even under the condition that the device A for deodorizing and drying is deformed in an almost hand drum-shape in section and the toes C — are nearly brought into close contact with each other, whereby the device A for deodorizing and drying is surrounded by the toes C—. In addition, since said particulate substances a—are housed in the cavit portion 3 forming the intermediate layer, the particulate substances a—are positioned in the vicinity of the roots of the toes C—to efficiently carry out the dehumidification by the particulate substances a—. This leads to the increased deodorizing effect and the effective prevention of ringworm.

In addition, although the device A for deodorizing and drying is formed in a circular shape in section in the above described preferred embodiment, various sectional shapes, such as a square shape and a rectangular shape, can be used.

Since the present invention has the above described construction, the following effects can be exhibited.

(1) Immediately after the device for deodorizing and drying was put between the toes the sense of incongruity is slightly felt but the intermediate layer is formed by the cavity portion and the particulate substances are housed in said cavity portion in the suitable quantity, in short, in the quantity corresponding to a part of the volume of the cavity portion with remaining spaces, so that the intermediate layer is easy to deform in a flat shape and the intermediate layer and the upper and lower fibrous layers are gradually smashed from both sides by the toes. As a result, the device for deodorizing and drying is plastically deformed in an almost hand drum-shape in section as a whole, so that the sense of incongruity can be eliminated and there is not the possibility that the toes are injured.

(2) Since the fibers constructing the upper and lower fibrous layers are orientated in the up and down direction, respectively, the ventilation exhibits the orientation, that is, the ventilation in the up and down direction is more notable than that in the lateral direction. Accordingly, the superior ventilation in the up and down direction can be kept even under the condition that the device for deodorizing and drying is deformed in an almost hand drum-shape in section and surrounded by the toes. In addition, since said particulate substances are housed in the cavity portion forming the intermediate layer, the particulate substances are positioned in the vicinity of the roots of the toes to efficiently carry out the humidification by the particulate substances. This leads to the increased drying and deodorizing effect in cooperation with the superior ventilation in the up and down direction.

What is claimed is:

1. A device for deodorizing and drying an area between toes, comprising:

two rod-shaped flexible fibrous elements, each element comprising a large number of fibers disposed parallel to the longitudinal axis of said element, an air- and water-permeable flexible shell member enclosing the rod-shaped surface of said flexible fibrous elements, the flexible fibrous elements being disposed in spaced apart end to end relation in the longitudinal direction for defining a cavity between the flexible fibrous elements, and particulate substances having a hygroscopic function housed in said cavity in a quantity corresponding to a part of a volume of said cavity, wherein the transverse dimension of said device is such that said device is capable of being inserted between toes.

* * * * *